United States Patent
Akashi et al.

(10) Patent No.: US 10,799,615 B2
(45) Date of Patent: Oct. 13, 2020

(54) ARTIFICIAL TISSUE AND METHOD FOR PRODUCING SAME

(71) Applicants: OSAKA UNIVERSITY, Osaka (JP); TOHOKU UNIVERSITY, Miyagi (JP)

(72) Inventors: Mitsuru Akashi, Suita (JP); Michiya Matsusaki, Toyonaka (JP); Michiaki Unno, Sendai (JP); Naoaki Sakata, Sendai (JP); Gumpei Yoshimatsu, Sendai (JP)

(73) Assignees: OSAKA UNIVERSITY, Osaka (JP); TOHOKU UNIVERSITY, Miyagi (JP)

(*) Notice: Subject to any disclaimer, the term of this patent is extended or adjusted under 35 U.S.C. 154(b) by 0 days.

(21) Appl. No.: 15/533,724

(22) PCT Filed: Dec. 7, 2015

(86) PCT No.: PCT/JP2015/084866
§ 371 (c)(1),
(2) Date: Jun. 7, 2017

(87) PCT Pub. No.: WO2016/093362
PCT Pub. Date: Jun. 16, 2016

(65) Prior Publication Data
US 2017/0333598 A1    Nov. 23, 2017

(30) Foreign Application Priority Data
Dec. 8, 2014  (JP) ................. 2014-248292

(51) Int. Cl.
| | | |
|---|---|---|
| *A61L 27/38* | (2006.01) | |
| *A61K 35/44* | (2015.01) | |
| *A61K 35/39* | (2015.01) | |
| *A61L 27/36* | (2006.01) | |
| *C12N 5/071* | (2010.01) | |
| *A61L 27/60* | (2006.01) | |
| *A61K 35/28* | (2015.01) | |
| *A61K 35/36* | (2015.01) | |
| *C12N 5/00* | (2006.01) | |

(52) U.S. Cl.
CPC .......... *A61L 27/3804* (2013.01); *A61K 35/39* (2013.01); *A61K 35/44* (2013.01); *A61L 27/3633* (2013.01); *A61L 27/3834* (2013.01); *A61L 27/3886* (2013.01); *A61L 27/60* (2013.01); *C12N 5/069* (2013.01); *C12N 5/0697* (2013.01); *A61K 35/28* (2013.01); *A61K 35/36* (2013.01); *C12N 5/00* (2013.01); *C12N 2502/1323* (2013.01); *C12N 2502/1358* (2013.01); *C12N 2502/22* (2013.01); *C12N 2503/04* (2013.01); *C12N 2533/52* (2013.01); *C12N 2533/90* (2013.01)

(58) Field of Classification Search
CPC ..... A61L 27/3804; A61L 27/60; A61K 35/28; C12N 2502/1323; C12N 2503/04; C12N 5/00
See application file for complete search history.

(56) References Cited

U.S. PATENT DOCUMENTS

| 4,678,566 | A | * | 7/1987 | Goosen | ............... | A61M 1/3472 |
|---|---|---|---|---|---|---|
| | | | | | | 210/143 |
| 5,116,753 | A | * | 5/1992 | Beattie | ................. | C12N 5/0676 |
| | | | | | | 435/34 |
| 5,516,681 | A | * | 5/1996 | Naughton | .............. | A61K 35/28 |
| | | | | | | 424/422 |
| 2010/0092433 | A1 | | 4/2010 | Levenberg et al. | | |
| 2013/0084266 | A1 | | 4/2013 | Ott et al. | | |
| 2013/0122586 | A1 | | 5/2013 | Kanamune et al. | | |
| 2014/0024010 | A1 | | 1/2014 | Akashi et al. | | |
| 2014/0050766 | A1 | | 2/2014 | Levenberg et al. | | |
| 2014/0289877 | A1 | * | 9/2014 | Taniguchi | .............. | A61K 35/28 |
| | | | | | | 800/8 |
| 2016/0177270 | A1 | | 6/2016 | Takebe et al. | | |

FOREIGN PATENT DOCUMENTS

| EP | 2 762 558 | 8/2014 |
|---|---|---|
| JP | 2012-115254 | 6/2012 |
| JP | 2013-521797 | 6/2013 |
| WO | 2012/133629 | 10/2012 |
| WO | 2013/047639 | 3/2015 |
| WO | 2015/012158 | 3/2017 |

OTHER PUBLICATIONS

Roobrouck et al. Concise Review: Culture Mediated Changes in Fate and/or Potency of Stem Cells. Stem Cells (2011), v29(4), p. 583-589 (Year: 2011).*

Rodemann et al. Tumor-Associated Fibroblasts and their Matrix, The Tumor Microenvironment 4 (2011), ISBN: 978-94-007-0658-3, eISBN: 978-94-007-0659-0, Ch. 2, p. 23-36. (Year: 2011).*

Johansson et al. Formation of Composite Endothelial Cell-Mesenchymal Stem Cell Islets, A Novel Approach to Promote Islet Revascularization. Diabetes (2008), v57, p. 2393-2401. (Year: 2008).*

Pisania et al. Quantitative analysis of cell composition and purity of human pancreatic islet preparations. Lab Invest (2010), v90(11), p. 1661-1675. (Year: 2010).*

Hughes et al. Matrigel: A complex protein mixture required for optimal growth of cell culture. Proteomics (2010), 10, 1886-1890 (Year: 2010).*

(Continued)

*Primary Examiner* — Sean C. Barron
(74) *Attorney, Agent, or Firm* — Wenderoth, Lind & Ponack, L.L.P.

(57) ABSTRACT

An artificial tissue containing pancreatic islet cells, fibroblasts and/or cells capable of differentiating, extracellular matrix, and vascular endothelial cells, in which the fibroblasts and/or the cells capable of differentiating, the extracellular matrix, and the vascular endothelial cells constitute a three-dimensional tissue structure in which a vascular network structure has been formed, and in which the three-dimensional tissue structure contains pancreatic islets constituted by aggregating ten or more of the pancreatic islet cells.

6 Claims, 4 Drawing Sheets

(56) References Cited

OTHER PUBLICATIONS

Tian et al. Small intestinal submucosa improves islet survival and function during in vitro culture. World J Gastroenterol (2005), 11(46), 7378-7383. (Year: 2005).*

Xu et al. Rapid Prototyping Three-Dimensional Cell/Gelatin/Fibrinogen Constructs for Medical Regeneration. Journal of Bioactive and Compatible Polymers (2007), 22, 363-377. (Year: 2007).*

Kawazoe et al. Three-dimensional Cultures of Rat Pancreatic RIN-5F Cells in Porous PLGA-collagen Hybrid Scaffolds. Journal of Bioactive and Compatible Polymers (2009), 24, 25-42. (Year: 2009).*

International Search Report dated Mar. 8, 2016 in International Application No. PCT/JP2015/084866.

Kaufman-Francis, K. et al., "Engineered Vascular Beds Provide Key Signals to Pancreatic Hormone-Producing Cells", Plos one, Jul. 12, 2012, 7, 7, e40741, Online ISSN: 1932-6203.

Nishiguchi, A. et al., "Effects of angiogenic factors and 3D-microenvironments on vascularization within sandwich cultures", Biomaterials, Mar. 18, 2014, 35, 4739-4748, ISSN: 0142-9612.

Baranski, J. D. et al., "Geometric control of vascular networks to enhance engineered tissue integration and function", PNAS, May 7, 2013, 110, 19, 7586-7591, Online ISSN: 1091-6490.

Sabra, G. and Vermette, P., "A 3D Cell Culture System: Separation Distance Between INS-1 Cell and Endothelial Cell Monolayers Co-Cultured in Fibrin Influences INS-1 Cells Insulin Secretion", Biotechnology and Bioengineering, Sep. 24, 2012, 110, 2, 619-627, Online ISSN: 1097-0290.

Asano, Y. et al., "Ultrastructure of blood and lymphatic vascular networks in three-dimensional cultured tissues fabricated by extracellular matrix nanofilm-based cell accumulation technique", Microscopy, Feb. 17, 2014, 63, 3, 219-226, Online ISSN: 2050-5701.

Gorden DL, et al. Transplantation. Feb. 15, 1997; 63(3):436-43 with exported figures.

Samikannu B, et al., "Dipeptidyl Peptidase IV Inhibition Activates CREB and Improves Islet Vascularization through VEGF-A/VEGFR-2 Signaling Pathway", Plos One Dec. 2013, vol. 8, Issue 12, e82639.

Sakata N, et al., "Bone Marrow Cell Cotransplantation with Islets Improves Their Vascularization and Function", Transplantation. Mar. 27, 2010; 89(6):686-693.

International Preliminary Report on Patentability dated Jun. 8, 2017 in corresponding International PCT Application No. PCT/JP2015/084866.

* cited by examiner

A

B

ARTIFICIAL TISSUE AND METHOD FOR PRODUCING SAME

TECHNICAL FIELD

The present invention relates to an artificial tissue and a method for producing the same.

BACKGROUND ART

Pancreatic islet transplantation is accepted as an effective method of treating patients of severe diabetes by improving blood glucose control. The pancreatic islet transplantation is performed by separating and extracting the islets of Langerhans from the pancreas of a donor and transplanting them into a recipient. However, the pancreatic islet transplantation has a problem of chronic shortage of donors, and it is further pointed out, as another problem, that the transplanted pancreatic islets fail to survive and are omitted by many reasons. As an important cause of lowering the survival of the pancreatic islets, ischemia occurring immediately after the transplantation has been mentioned.

Various studies have been conducted to improve a success rate of the pancreatic islet transplantation. One of such a method is to promote vascularization in the transplanted pancreatic islets using an angiogenesis factor and the like (Non Patent Documents 1 to 3). Non Patent Document 1 discloses that the pancreatic islets are cultured in the presence of the angiogenesis factor such as VEGF to promote vascularization. Non Patent Document 2 discloses a method in which the angiogenesis factor is induced by administration of an agent to promote vascularization in the pancreatic islets. Non Patent Document 3 discloses a method in which the pancreatic islets are transplanted together with cells that secrete the angiogenesis factor, such as mesenchymal stem cells, to promote vascularization.

CITATION LIST

Non Patent Document

Non Patent Document 1: Gorden D L, et al. Transplantation. 1997 Feb. 15; 63(3): 436-43
Non Patent Document 2: Samikannu B, et al. Plos One 2013 December, Volume 8, Issue 12, e82639
Non Patent Document 3: Sakata N, et al. Transplantation. 2010 March 27; 89(6): 686-693

SUMMARY OF THE INVENTION

Technical Problem

The present invention provides an artificial tissue containing vascularized pancreatic islets.

Solution to Problem

In one or more of embodiments, the present invention relates to an artificial tissue containing pancreatic islet cells, fibroblasts and/or cells capable of differentiating, extracellular matrix, and vascular endothelial cells, in which the fibroblasts and/or the cells capable of differentiating, the extracellular matrix, and the vascular endothelial cells constitute a three-dimensional tissue structure in which a vascular network has been formed, and in which the three-dimensional tissue structure contains pancreatic islets constituted by assembling a plurality of the pancreatic islet cells.

In one or more of embodiments, the present invention relates to a method for production of an artificial tissue, comprising steps of: forming a three-dimensional tissue structure by culturing fibroblasts and/or cells capable of differentiating, vascular endothelial cells, and extracellular matrix; and culturing pancreatic islet cells arranged on the three-dimensional tissue structure at the same time of or after forming the three-dimensional tissue structure, in which the fibroblasts and/or the cells capable of differentiating, the extracellular matrix, and the vascular endothelial cells constitute the three-dimensional tissue structure in which a vascular network has been formed, and in which the three-dimensional tissue structure contains pancreatic islets constituted by assembling a plurality of the pancreatic islet cells.

Advantageous Effects of Invention

According to the present invention, an artificial tissue containing vascularized pancreatic islets can be provided.

BRIEF DESCRIPTION OF DRAWINGS

FIG. 2A shows the insulin secretion amounts in a low glucose medium (Low) and a high glucose medium (High) and FIG. 2B shows ratios of the insulin secretion amounts (stimulation index) in Examples 1 to 3 and Comparative example.

DESCRIPTION OF EMBODIMENTS

Figure 1:
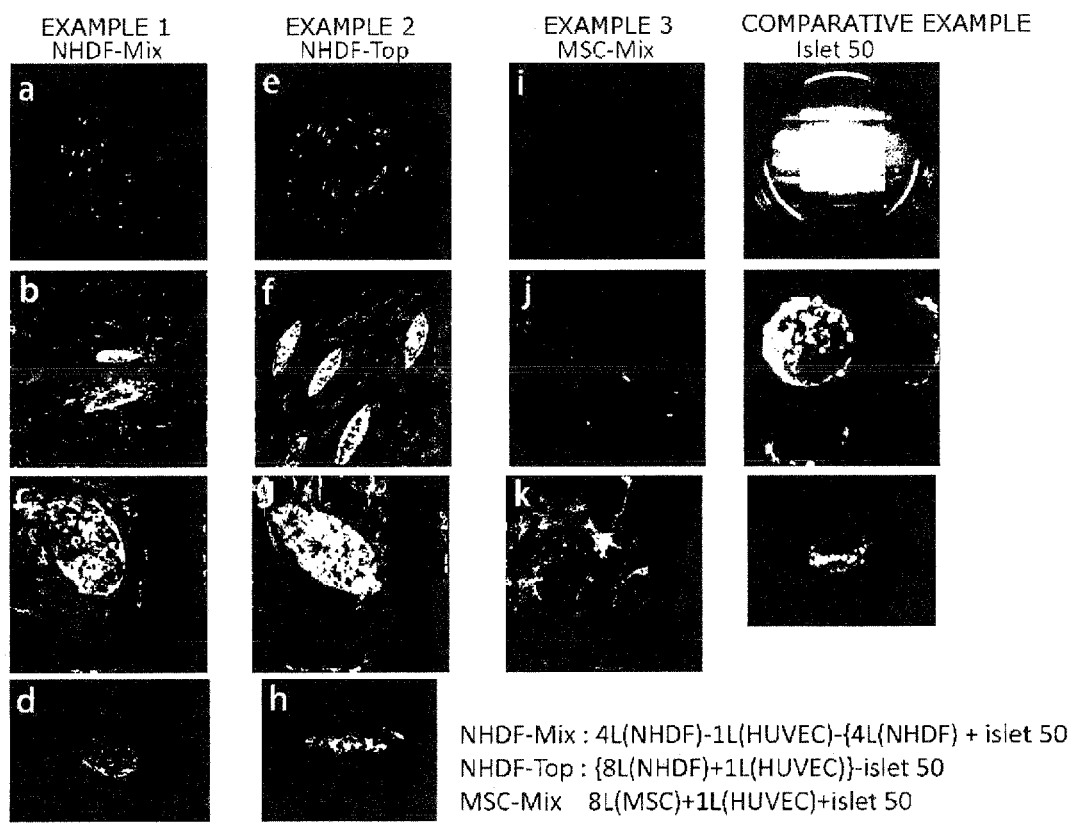
FIG. 1 shows images, taken by a laser confocal microscope, of artificial tissues in Examples 1 to 3 and cultured products of pancreatic islets in Comparative example.

From the viewpoint that the primary reason of lowering the survival of the pancreatic islets is ischemia occurring immediately after the transplantation, caused by taking time to form a vascular network between the transplanted pancreatic islets and the transplantation site, the present invention has been made based on the finding that the vascular network between the transplanted pancreatic islets and the transplantation site can be quickly formed to quickly restore a blood flow to the transplanted pancreatic islets by transplanting vascularized pancreatic islets. Further, the present invention has been made based on the finding that the vascularized pancreatic islets can be obtained by culturing the pancreatic islets with fibroblasts and/or cells capable of differentiating, vascular endothelial cells, and extracellular matrix.

According to the present invention, in one or more of embodiments, the vascular network between the transplantation site and the transplanted pancreatic islets can be quickly formed to quickly generate a blood flow between the transplantation site and the transplanted pancreatic islets, thus it is expected that the occurrence of ischemia shortly after the transplantation can be prevented and that the survival of the pancreatic islets can be improved. According to the present invention, in one or more of embodiments, a blood flow can be restored quicker than a conventional angiogenesis-promoting method performed after the transplantation. In one or more of embodiments, the present invention can eventually lead to an improvement in the transplantation efficiency and transplantation performance. Further, as a result, in one or more of embodiments, the present invention makes it possible to use a tissue where the pancreatic islets hardly survive due to less blood flows, such as a subcutaneous tissue and a muscle, despite the fact that such a tissue can provide a safer transplantation site, as an effective transplantation site, thereby enabling to replace the current intrahepatic transplantation.

In one or more of embodiments, the present invention can provide an artificial tissue excellent in secreting insulin in response to glucose load.

In the present invention, the term "artificial tissue" refers to a tissue structure containing the pancreatic islets and a vascular network structure. In the present invention, the term "vascularized pancreatic islets" refers to the pancreatic islets in which a vascular network structure is formed or the pancreatic islets in which angiogenesis is established. The vascularized pancreatic islets are preferably the pancreatic islets in which the vascular network structure is formed adjacently around the pancreatic islets, more preferably the pancreatic islets in which the blood can circulate through the vascular network structure formed around the pancreatic islets. In the present invention, the term "vascular network structure" refers to a hollow tubular structure formed by the vascular endothelial cells, preferably a blood vessel network, more preferably a structure formed in a net-like network, similar to a capillary vascular network.

In one or more of embodiments, the artificial tissue of the present invention can serve as a functional or structural model of the pancreatic islets or the pancreas. In one or more of embodiments, the artificial tissue of the present invention may include a model capable of reproducing a function of the pancreatic islets, a model required for reproducing a function of the pancreatic islets, and the like. Further, in one or more of embodiments, the artificial tissue of the present invention can be used for pancreatic islet transplantation.

In one or more of embodiments, cells used in the present invention may be human cells or nonhuman animal cells. In one or more of embodiments, the cells may be derived from mesenchymal stem cells, embryonic stem cells, induced pluripotent stem cells, and the like. In one or more of embodiments, the cells may be cultured cells. In one or more of embodiments, examples of the cultured cells include primary culture cells, sub-cultured cells, and cells from a cell line.

[Artificial Tissue]

In one or more of embodiments, the present invention relates to an artificial tissue containing pancreatic islet cells, fibroblasts and/or cells capable of differentiating, extracellular matrix, and vascular endothelial cells (hereinafter referred to as an "artificial tissue of the present invention"). In one or more of embodiments, the artificial tissue of the present invention contains the vascular endothelial cells which form a vascular network structure. Further, in the artificial tissue of the present invention, the pancreatic islets are formed by aggregating a plurality of the pancreatic islet cells, preferably 10 or more of the pancreatic islet cells. Thus, in one or more of embodiments, in the artificial tissue of the present invention, the fibroblasts and/or the cells capable of differentiating, the extracellular matrix, and the vascular endothelial cells constitute a three-dimensional tissue structure in which the vascular network has been formed and the three-dimensional tissue structure contains the pancreatic islets constituted by aggregating the plurality of the pancreatic islet cells, preferably 10 or more of the pancreatic islet cells. It is noted that the "fibroblasts and/or cells capable of differentiating" may mean fibroblasts, cells capable of differentiating, or both fibroblasts and cells capable of differentiating.

In one or more of embodiments, the pancreatic islets refer to an aggregate of the pancreatic islet cells constituted by aggregating a plurality of the pancreatic islet cells, preferably 10 or more of the pancreatic islet cells. In one or more of embodiments, the "pancreatic islet cells" of the present invention refer to pancreatic endocrine cells capable of secreting insulin, glucagon, and the like, preferably pancreatic endocrine cells capable of adjusting a blood glucose level by secreting insulin, glucagon, and the like. In one or more of embodiments, the pancreatic islets are an aggregate of the pancreatic islet cells, including spheroidal pancreatic islet cells, preferably capable of secreting insulin or inducing insulin secretion, more preferably having a function closer to an in vivo pancreatic islet function, further preferably having a function equivalent to the in vivo pancreatic islet function. In one or more of embodiments, the pancreatic islets contain 1 or more, 10 or more, 20 or more, 30 or more, 40 or more, 50 or more, 60 or more, or 70 or more of the pancreatic islet cells. The upper limit of the number of the pancreatic islet cells is not limited, however, in one or more of embodiments, it may be 1,000 or less.

From the viewpoint of facilitating the supply of oxygen, nutrients, and the like via the vascular network structure, in one or more of embodiments, the pancreatic islets are formed so as to contact with the vascular network structure, preferably formed so as to be surrounded by the vascular network structure.

In one or more of embodiments, the artificial tissue of the present invention contains 1 or more, 5 or more, 10 or more, 15 or more, 20 or more, 25 or more, 30 or more, or 45 or more of the pancreatic islets. The upper limit of the number of the pancreatic islets is not limited, however, in one or more of embodiments, it may be 1,000 or less.

In one or more of embodiments, the extracellular matrix may contain a substance capable of performing the above-mentioned roles in an in vitro cell culture, an artificially synthesized substance or a part thereof. In one or more of embodiments, specific examples of the extracellular matrix include fibronectin, gelatin, collagen, laminin, and polylysine. The extracellular matrix is not limited to these examples and includes those disclosed in JP 2007-228921A (JP 4919464 B) and JP 2012-115254A. When the artificial tissue of the present invention is transplanted to a living body, the extracellular matrix is preferably constituted with a substance showing no significant toxicity to the living body, such as fibronectin, gelatin, collagen, laminin, and polylysine.

One kind or two or more kinds of the extracellular matrix may be used. In one or more of embodiments, as a combination of the different kinds of the extracellular matrix, a combination of a first substance and a second substance interacting with the first substance can be mentioned. In one or more of embodiments, examples of the combination of the first substance and the second substance include a combination of a polymer having an RGD sequence and a polymer interacting with the polymer having an RGD sequence or a combination of a polymer that is positively charged and a polymer that is negatively charged. In one or more of embodiments, specific examples of the combination of the first substance and the second substance include combinations of fibronectin and gelatin, fibronectin and ε-polylysine, fibronectin and hyaluronic acid, fibronectin and dextran sulfate, fibronectin and heparin, and laminin and gelatin.

In one or more of embodiments, the artificial tissue of the present invention may contain cells other than the pancreatic islet cells, the fibroblasts and/or the cells capable of differentiating, and the vascular endothelial cells. In one or more of embodiments, examples of such cells include cells constituting an organ other than the pancreas, such as hepatocytes and kidney cells.

[Method for Production of Artificial Tissue]

In one or more of embodiments, the present invention relates to a method for production of an artificial tissue containing pancreatic islets, the method comprising steps of: forming a three-dimensional tissue structure by culturing fibroblasts and/or cells capable of differentiating, vascular endothelial cells, and extracellular matrix; and culturing pancreatic islet cells arranged on the three-dimensional tissue structure at the same time of or after forming the three-dimensional tissue structure (hereinafter, also referred to as a "method for production of the present invention"). The method for production of the present invention enables to produce the artificial tissue containing the pancreatic islets, in which the fibroblasts and/or the cells capable of differentiating, the extracellular matrix, and the vascular endothelial cells constitute the three-dimensional tissue structure in which a vascular network structure has been formed, and in which the three-dimensional tissue structure contains the pancreatic islets constituted by aggregating ten or more of the pancreatic islet cells.

In one or more of embodiments, the method for production of the present invention enables to produce the artificial tissue containing the pancreatic islets and the vascular network structure. In one or more of embodiments, the method for production of the present invention enables to produce a tissue in which the vascular network structure is formed around the pancreatic islets, preferably a tissue in which the blood can circulate in the pancreatic islet cells through the vascular network structure. The method for production of the present invention can facilitate the production of the artificial tissue of the present invention.

In one or more of embodiments, examples of the cells capable of differentiating include stem cells such as mesenchymal stem cells (MSC), embryonic stem cells (ES cells), and induced pluripotent stem cells (iPS cells). The cells capable of differentiating may be differentiated, for example, into fibroblasts or other cell types.

The method for production of the present invention comprises the step of forming the three-dimensional tissue structure by culturing the fibroblasts and/or the cells capable of differentiating, the vascular endothelial cells, and the extracellular matrix.

In one or more of embodiments, the three-dimensional tissue structure can be formed by coating the cells with coating membranes containing the extracellular matrix and culturing coated cells arranged in a three dimension (a method using coated cells). Further, in another method, the three-dimensional tissue structure can be formed by culturing cells in such a manner that the cells (one layer) and the extracellular matrix are alternately laminated (a method using LBL). The method using coated cells and the method using LBL may be combined. In one or more of embodiments, the method using coated cells can be performed based on Examples, a method disclosed in JP 2012-115254A, and the like. In one or more of embodiments, the method using LBL can be performed based on a method disclosed in JP 2007-228921A (JP 4919464 B) and the like.

The method for production of the present invention comprises the step of culturing the pancreatic islet cells arranged on the three-dimensional tissue structure at the same time of or after forming the three-dimensional tissue structure. In one or more of embodiments, the pancreatic islet cells may be mixed with the fibroblasts and/or the cells capable of differentiating, and arranged in the three-dimensional tissue structure at the same time of forming the three-dimensional tissue structure, or arranged on the three-dimensional tissue structure after forming the three-dimensional tissue structure.

In one or more of embodiments, the three-dimensional tissue structure can be formed by: culturing the fibroblasts and/or the cells capable of differentiating to form a cell layer; culturing the vascular endothelial cells arranged on the cell layer thus formed to form one layer of the vascular endothelial cells; and then mixing and culturing the fibroblasts and/or the cells capable of differentiating and the pancreatic islet cells arranged on the layer of the vascular endothelial cells. In another method, the three-dimensional tissue structure can be formed by: culturing the fibroblasts and/or the cells capable of differentiating to form a cell layer; culturing the vascular endothelial cells arranged on the cell layer to form one layer of the vascular endothelial cells; culturing the fibroblasts and/or the cells capable of differentiating arranged on the layer of the vascular endothelial cells to form a laminated body in which a vascular network structure is formed; and then culturing the pancreatic islet cells arranged on the laminated body. In another method, the three-dimensional tissue structure can be formed by mixing and culturing the fibroblasts and/or the cells capable of differentiating, the vascular endothelial cells, and the pancreatic islet cells. Further, in another method, the three-dimensional tissue structure can be formed by: mixing and culturing the fibroblasts and/or the cells capable of differentiating and the vascular endothelial cells; and then culturing the pancreatic islet cells arranged on the mixed culture.

In one or more of embodiments, the method for production of the present invention includes using the pancreatic islets constituted by aggregating a plurality of the pancreatic islet cells, preferably 10 or more of the pancreatic islet cells, as the pancreatic islet cells. In one or more of embodiments, examples of the pancreatic islets include isolated pancreatic islets and a spheroid/cell aggregate reconstituted by the pancreatic islet cells. In one or more of embodiments, the method for production of the present invention comprises a step of culturing the fibroblasts and/or the cells capable of differentiating, the vascular endothelial cells, the extracellular matrix, and the pancreatic islets.

In one or more of embodiments, the number of the pancreatic islets to be arranged is 1 or more, 5 or more, 10 or more, 15 or more, 20 or more, 25 or more, 30 or more, or 45 or more. The upper limit of the number of the pancreatic islets is not limited, however, in one or more of embodiments, it may be 1,000 or less.

Hereinafter, the present invention will be described in detail by way of preferred embodiments. However, it should be noted that the present invention is not limited to the following embodiments.

Embodiment 1

First, fibroblasts and vascular endothelial cells coated with coating membranes containing extracellular matrix (hereinafter, also referred to as "coated fibroblasts" and "coated vascular endothelial cells", respectively) are prepared. In one or more of embodiments, the coating membranes containing extracellular matrix can be formed by alternately laminating fibronectin and gelatin.

The coated fibroblasts are arranged on a base material, such as a Cell Culture Insert, for culturing. The coated fibroblasts are arranged on the base material so as to be laminated in 4 layers or more, preferably 5, 8, or 10 layers or more. In one or more of embodiments, a cell density of the fibroblasts at the time of being arranged is $1 \times 10^2$ to $1 \times 10^9/cm^3$, $1 \times 10^4$ to $1 \times 10/cm^3$, or $1 \times 10^5$ to $1 \times 10^7/cm^3$.

In one or more of embodiments, cell culture is performed by adding a medium. In one or more of embodiments, examples of the medium include an Eagle's MEM medium, a Dulbecco's Modified Eagle's medium (DMEM), a Modified Eagle's medium (MEM), a Minimum Essential medium, an RDMI medium, and a GlutaMax medium. In one or more of embodiments, the medium is preferably added with serum. In one or more of embodiments, a culturing temperature is 37° C. In one or more of embodiments, a culturing time is 6 to 24 hours.

Next, the coated vascular endothelial cells are arranged on a laminated body formed by the fibroblasts for culturing. The coated vascular endothelial cells are arranged so as to form one layer of the vascular endothelial cells. In one or more of embodiments, a cell density of the vascular endothelial cells at the time of being arranged is $1 \times 10^2$ to $1 \times 10^9/cm^3$, $1 \times 10^4$ to $1 \times 10^8/cm^3$, or $1 \times 10^5$ to $1 \times 10^7/cm^3$. The culture conditions are as described above.

Subsequently, a mixture of the coated fibroblasts and isolated pancreatic islets are arranged on the vascular endothelial cells for culturing. The number of the pancreatic islets to be arranged, the cell density of the coated fibroblasts, and the culture conditions are as described above. In this manner, an artificial tissue in which a capillary vessel-like structure is formed around the pancreatic islets can be formed.

Embodiment 2

First, coated fibroblasts and coated vascular endothelial cells are prepared. The coated fibroblasts and the coated vascular endothelial cells are mixed and arranged on a base material, such as a Cell Culture Insert, for culturing. The cell density and the culture conditions of the coated fibroblasts and the coated vascular endothelial cells are the same as in Embodiment 1. In this manner, a laminated body having a vascular network structure is formed.

Next, isolated pancreatic islets are arranged on the laminated body thus formed for culturing. The number of the pancreatic islets to be arranged and the culture conditions are the same as in Embodiment 1. In this manner, an artificial tissue in which a capillary vessel-like structure is formed around the pancreatic islets can be formed.

Embodiment 3

First, mesenchymal stem cells coated with coating membranes containing extracellular matrix (hereinafter referred to as "coated mesenchymal stem cells") are prepared.

Next, the coated mesenchymal stem cells, coated vascular endothelial cells, and isolated pancreatic islets are mixed and arranged on a base material, such as a Cell Culture Insert, for culturing. The coated mesenchymal stem cells have the same cell density as the coated fibroblasts. The cell density of the coated vascular endothelial cells, the number of the pancreatic islets, and the culture conditions are the same as in Embodiment 1. In this manner, an artificial tissue in which a capillary vessel-like structure is formed around the pancreatic islets can be formed.

The present invention may relate to one or more of embodiments below.

[1] An artificial tissue containing pancreatic islet cells, fibroblasts and/or cells capable of differentiating, extracellular matrix, and vascular endothelial cells, wherein:

the fibroblasts and/or the cells capable of differentiating, the extracellular matrix, and the vascular endothelial cells constitute a three-dimensional tissue structure in which a vascular network structure has been formed; and the three-dimensional tissue structure contains pancreatic islets constituted by aggregating a plurality of the pancreatic islet cells.

[2] The artificial tissue according to [1], wherein the pancreatic islets are constituted by aggregating 10 or more of the pancreatic islet cells.

[3] The artificial tissue according to [1] or [2], wherein the pancreatic islets are arranged adjacent to the vascular network structure.

[4] The artificial tissue according to any of [1] to [3] containing 5 or more of the pancreatic islets.

[5] A method for production of an artificial tissue, comprising steps of:

forming a three-dimensional tissue structure by culturing fibroblasts and/or cells capable of differentiating, vascular endothelial cells, and extracellular matrix; and culturing pancreatic islet cells arranged on the three-dimensional tissue structure at the same time of or after forming the three-dimensional tissue structure, wherein:

the fibroblasts and/or the cells capable of differentiating, the extracellular matrix, and the vascular endothelial cells constitute the three-dimensional tissue structure in which a vascular network structure has been formed; and the three-dimensional tissue structure contains pancreatic islets constituted by aggregating a plurality of the pancreatic islet cells.

[6] The method for production according to [5], wherein the fibroblasts and/or the cells capable of differentiating have surfaces coated with coating membranes containing the extracellular matrix.

[7] The method for production according to [5] or [6], wherein the vascular endothelial cells have surfaces coated with coating membranes containing the extracellular matrix.

[8] The method for production according to any of [5] to [7], wherein the pancreatic islets constituted by aggregating 10 or more of the pancreatic islet cells are used as the pancreatic islet cells.

[9] The method for production according to any of [5] to [8], comprising a step of mixing and culturing the fibroblasts and/or the cells capable of differentiating coated with coating membranes, the vascular endothelial cells coated with coating membranes, and the pancreatic islet cells.

[10] The method for production according to any of [5] to [8], comprising steps of culturing the fibroblasts and/or the cells capable of differentiating coated with coating membranes, and the vascular endothelial cells coated with coating membranes; and culturing the pancreatic islet cells arranged on a cell layer formed by the culture.

[11] The method for production according to any of [5] to [8], comprising steps of arranging and culturing the fibroblasts and/or the cells capable of differentiating coated with coating membranes; culturing the vascular endothelial cells coated with coating membranes arranged on a cell layer formed by the culture; and mixing and culturing the fibroblasts and/or the cells capable of differentiating coated with coating membranes, and the pancreatic islet cells arranged on the vascular endothelial cells.

[12] The method for production according to any of [5] to [11], wherein stem cells are used as the cells capable of differentiating.

[13] The method for production according to any of [5] to [12], wherein the artificial tissue according to any of [1] to [4] is produced.

Hereinafter, the present invention will be further described by way of Examples and Comparative example. However, it should be noted that Examples described below are not intended to limit the interpretation of the present invention.

The following reagents, culture inserts, media, and cells were used in Examples.

<Human Fibronectin/Tris Solution>

Fibronectin (BNF) (manufactured by Sigma-Aldrich Co. LLC., (F-2006, 5 mg), Fibronectin from Human plasma) was dissolved in 50 mM Tris-HCl (pH=7.4) to prepare a 0.2 mg/ml FN/Tris solution (5 mg of fibronectin added to 25 ml of Tris-HCl). This solution was further diluted five times with 50 mM Tris-HCl (pH=7.4) to prepare a 0.04 mg/mL FN/Tris solution. Hereafter, this solution is referred to as an "FN-Tris solution".

Molecular weight=450 kDa, water-soluble, having a collagen binding site.

<Gelatin/Tris Solution>

Gelatin (manufactured by Wako Pure Chemical Industries, Ltd., 077-3155, 500 g) was dissolved in 50 mM Tris-HCl (pH=7.4) to prepare a 0.2 mg/ml gelatin solution. This solution was further diluted five times with 50 mM Tris-HCl (pH=7.4) to prepare a 0.04 mg/ml G/Tris solution. Hereafter, this solution is referred to as a "G-Tris solution".

<Tris-HCl>

A 50 mM 2-Amino-2-hydroxymethyl-1,3-propanediol Hydrochloride (Tris-HCl) (manufactured by Wako Pure Chemical Industries, Ltd., 012-17455) solution was prepared, adjusted to pH 7.4, and sterilized by the autoclave.

<Culture Inserts>

Manufactured by Corning Incorporated, 3470, 24 well, material: PET, pore size: 0.4 μm, pore density: $1.6 \times 10^6/cm^2$, bottom area: 0.33 $cm^2$ (different pore sizes may be used)

<Media>

DMEM, high glucose: manufactured by Wako Pure Chemical Industries, Ltd., 043-30085 (added with 10% FBS and 1% antibiotics)

Vascular endothelial cell culture kit: EGM-2 MV manufactured by Lonza, CC-3202

<Cells>

Normal human dermal fibroblasts (NHDF): manufactured by Lonza, CC-2509 (neonatal)

Human umbilical vein endothelial cells (HUVEC): manufactured by Lonza, CC-2517

Human mesenchymal stem cells from bone marrow (BM-MSC): manufactured by PromoCell GmbH, C-12974

Mouse pancreatic islets: gift from Naoaki Sakata, National University Corporation Tohoku University

[Preparation of Coated Cells]

NHDF were coated with FN-G thin membranes by the following procedures. NHDF ($1 \times 10^7$ cells) were added with 1 ml of the FN-Tris solution, incubated for 1 min, and spun down by centrifugation at 420×g (2500 rpm) for 1 min to remove a supernatant. The cells were rinsed for 1 min by adding 1 ml of the Tris-HCl and spun down by centrifugation at 420×g (2500 rpm) for 1 min to remove a supernatant. Subsequently, the same operations were repeated with the G-Tris solution in place of the FN-Tris solution. If each incubation and rinsing operation is considered as one step, a total of 9 steps ($(FN/G)_4$ FN) were performed to form the thin FN-G membranes on the surfaces of NHDF. Coated NHDF were thus prepared.

Coated HUVEC or coated BM-MSC was prepared by forming the thin FN-G membranes on these cells in the same manner except that HUVEC or BM-MSC were used instead of NHDF.

Example 1

[Production of Artificial Tissue]

A culture insert was added with 100 of the 0.2 mg/mL FN/Tris solution and incubated for 15 min or longer. The culture insert was then rinsed with Tris-HCl to form an FN base membrane on a surface of the insert.

The coated NHDF suspended in DMEM (10% FBS) were seeded in the insert on which the FN base membrane was formed at the cell concentration of $4 \times 10^5$ cells/well and supplied with a medium (inside: 0.3 mL, outside: 1 mL). After incubating the cells at 37° C. for 1 to 2 hours, 1 mL of the medium was further added to the outside of the insert to connect the medium between the inside and the outside of the insert. After 24-hour incubation, a laminated tissue (4 layers, NHDF tissue) was obtained.

The coated HUVEC suspended in DMEM (10% FBS) were seeded at the cell concentration of $3 \times 10^4$ cells/well on the NHDF tissue. After 24-hour culture, a laminated tissue (4 layers of NHDF-1 layer of HUVEC) was obtained.

The coated NHDF at $4 \times 10^5$ cells/well and isolated pancreatic islets at 50 islets/well were mixed and suspended in DMEM (10% FBS). A mixture was seeded on the laminated tissue and cultured for 24 hours to obtain an artificial tissue.

Measurement of an amount of insulin secreted from the obtained artificial tissue and histological observation of the artificial tissue were performed.

The insulin secretion amounts were measured by applying glucose solutions at different concentrations to the artificial tissue and measuring the amounts of insulin secreted in the solution by the ELISA method. First, the artificial tissue was pre-incubated with a low glucose medium (3.3 mM glucose (60 mg/dl)) by the following procedures.

After incubating with 10 mL of the low glucose medium for 1 hour, the artificial tissue was rinsed 3 times with 5 mL of the low glucose medium. After completing the pre-incubation, the artificial tissue was cultured in 10 mL of the low glucose medium for 1 hour, and then the supernatant was recovered (sample L).

After recovering the supernatant, the artificial tissue was cultured with 10 mL of a high glucose medium (16.5 mM glucose (60 mg/dl)) for 1 hour and the supernatant was recovered (sample H).

The supernatants thus recovered (sample L and sample H) were frozen with liquid nitrogen and stored at −80° C.

After removing the supernatant, the artificial tissue was rinsed with PBS and fixed with 10% formalin for 3 hours for preparing tissue sections (for fluorescence observation, fixation was performed with 4% PFA for 15 min). The tissue sections were subjected to HE staining, immunostaining, and the like to perform the histological observation.

The amounts of insulin secreted in the recovered supernatants were measured with a mouse insulin ELISA kit according to the attached manual. An ELISA kit, Lbis Insulin-Mouse (AKRIN-031) manufactured by SHIBAYAGI Co., Ltd., was used for the measurement. Specifically, biotin-conjugated anti-insulin antibodies were disposed in an antibody-immobilized plate, and samples were further added in the plate and incubated for 2 hours at the room temperature. After rinsing wells, peroxidase-avidin conjugates were added in the plate and incubated for 30 min at the room temperature. After rinsing, reaction was carried out in a color developing solution for 30 min. After completing the reaction, the plate was subjected to a plate reader (absorbance at 450 nm and 620 nm). The obtained data were used to calculate the insulin secretion amounts in each sample based on data obtained using the standard concentrations.

Further, a stimulation index (SI) represented by the following formula:

$$SI = \text{(amount of secreted insulin with high glucose concentration)} / \text{(amount of secreted insulin with low glucose concentration)}$$

was calculated based on the obtained insulin secretion amounts.

As a control, recovery of the supernatant for measuring the amount of insulin and measurement of the amount of insulin were performed in the same manner as described above except that the pancreatic islets were not seeded.

Example 2

A mixture of coated NHDF at $8 \times 10^5$ cells/well and coated HUVEC at $3 \times 10^4$ cells/well was seeded in an insert on which the FN base membrane was formed and cultured for 24 hours. Isolated pancreatic islets at 50 islets/well were seeded on an obtained laminated tissue and cultured for 1 day to obtain an artificial tissue. The obtained artificial tissue was subjected to the measurement of the insulin secretion amount and the histological observation in the same manner as in Example 1.

Example 3

Coated BM-MSC at $8 \times 10^5$ cells/well, coated HUVEC at $3 \times 10^4$ cells/well, and isolated pancreatic islets at 50 islets/well were mixed, seeded in an insert on which the FN base membrane was formed, and cultured for 1 day to obtain an artificial tissue. The obtained artificial tissue was subjected to the measurement of the insulin secretion amount and the histological observation in the same manner as in Example 1.

Comparative Example

The measurement of the insulin secretion amount and the histological observation were performed in the same manner as in Example 1 except that the pancreatic islets were seeded in an untreated insert.

(Controls 1-3)

Artificial tissues were produced in the same manner as in Examples 1 to 3 except that the pancreatic islets were not used.

Figure 2:
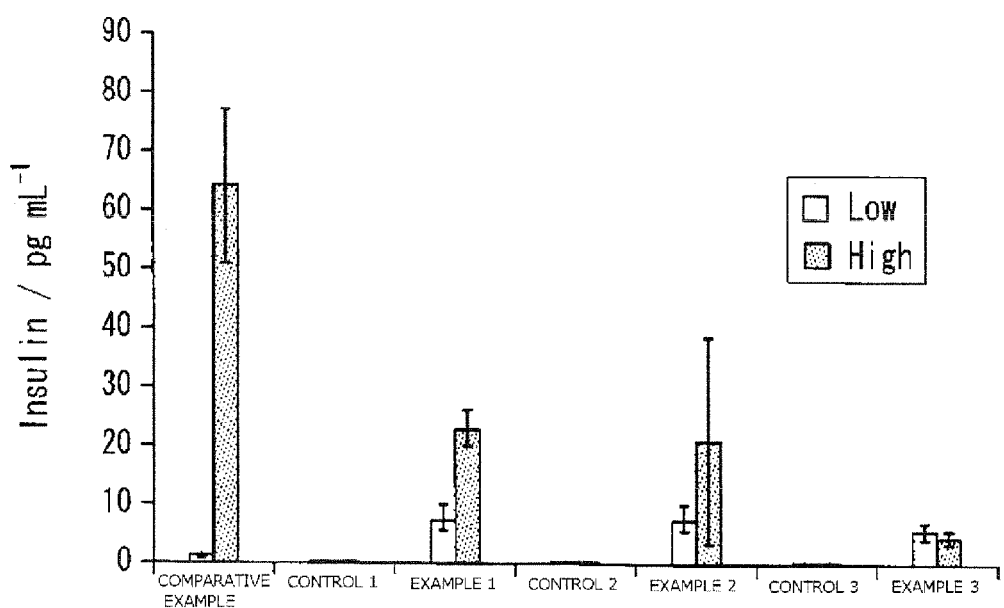
FIG. 2 shows graphs depicting measurement results of insulin secretion amounts in Examples 1 to 3, Controls 1 to 3, and Comparative example, where
Figure 2:
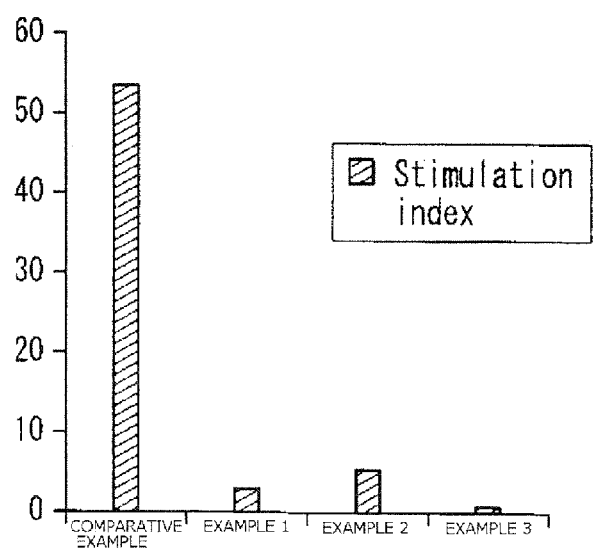

The results thus obtained are shown in FIG. 1 and FIG. 2. FIG. 1 shows images, taken by a laser confocal microscope, of the artificial tissues in Examples 1 to 3 and the cultured products of the pancreatic islets in Comparative example. FIG. 2 shows graphs depicting the measurement results of the insulin secretion amounts in Examples 1 to 3, Controls 1 to 3, and Comparative example, where FIG. 2A shows the insulin secretion amounts in the low glucose medium (Low) and the high glucose medium (High) and FIG. 2B shows the stimulation indexes.

The pancreatic islets in Examples 1 to 3 are appeared in a rice grain-like shape in the images in FIG. 1 (FIGS. 1*a, f* and *g*). As shown in FIG. 1, it was observed that, in the artificial tissues in Examples 1 to 3, the vascular network structure was formed around the pancreatic islets and the pancreatic islets, whether located in the inside or on the surface of the tissue, maintained an excellent morphology. It was observed that the artificial tissues in Examples 1 and 2 contained more pancreatic islets than the artificial tissue in Example 3 (FIG. 1*b-c, g-h,* and *k-l*).

As shown in FIGS. 2A and B, it was confirmed that the artificial tissues in Examples 1 to 3 could secrete insulin in response to the concentration change of glucose although the total amounts of secreted insulin were reduced as compared with that in Comparative example 1 (the pancreatic islets alone).

Example 4

The present experiment was conducted to test if the artificial tissue of the present invention could actually survive and secrete insulin after being transplanted to a living body.

Figure 3:
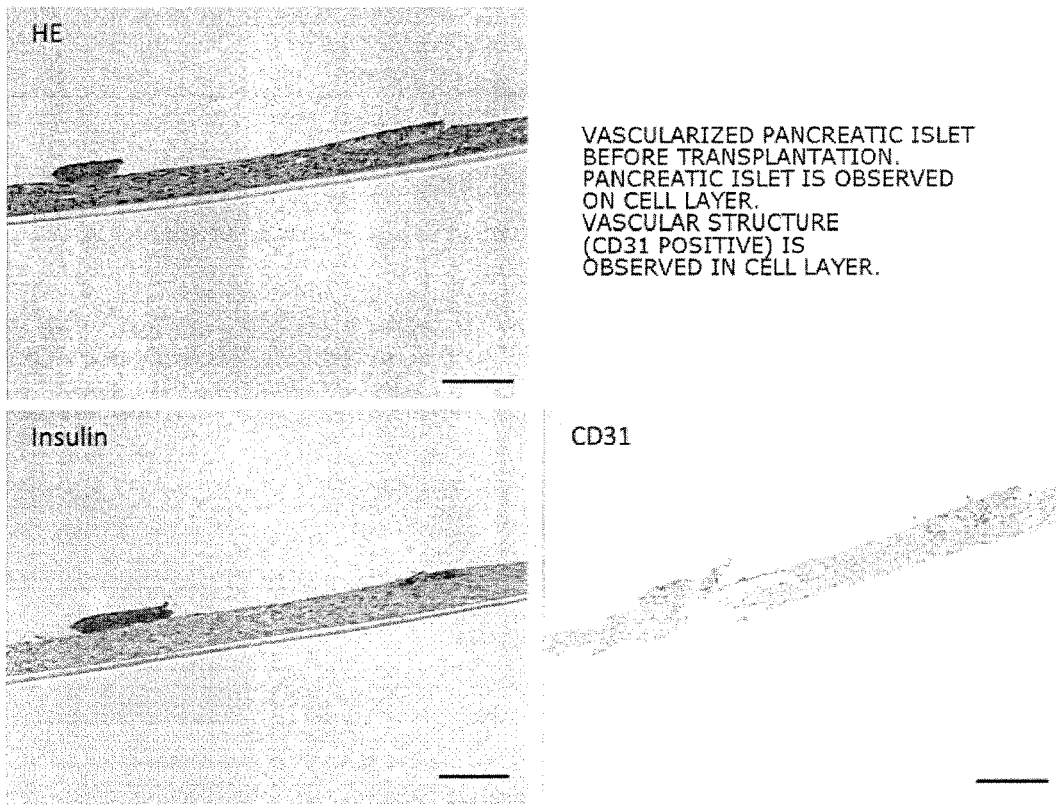
FIG. 3 shows section images of an artificial tissue used for transplantation to a mouse, visualized by hematoxylin-eosin (HE) staining (A), immunostaining for insulin (B), and immunostaining for CD31 (C). Arrows in FIG. 3C indicate CD31-staining positive areas. The bar in each panel is 100 μm long.

The artificial tissue was obtained according to the method described in Example 1. FIG. 3A shows the section of the artificial tissue stained by hematoxylin-eosin (HE) according to the routine procedure. Further, FIGS. 3B and 3C show the artificial tissues immuno-stained for insulin and CD31, respectively, according to the routine procedure. It was confirmed that the pancreatic islets were formed on a cell layer of the obtained artificial tissue and secreted insulin, and the vascular structure was formed on the cell layer.

The artificial tissue was transplanted in the mouse abdominal wall fat. The procedures were as follows.

The artificial tissue was produced on a 24-well Transwell plate in the same manner as described in Example 1. The diameter of the obtained artificial tissue was 6.5 mm. The artificial tissue contained 150 pancreatic islets derived from BALB/c mice. After confirming that the obtained artificial tissue increased the insulin secretion amount in response to glucose load, which is applied to the obtained artificial tissue, according to the method described in Example 1, the artificial tissue was transplanted into the mouse.

A streptozotocin-induced diabetic, severe combined immunodeficient mouse (SCID mouse) was subject to laparotomy under inhalation anesthesia, and the fat tissue attached to the testicles was extended. The artificial tissue removed from the Transwell plate together with the membranes was placed on the extended fat tissue. Finally, the artificial tissue, covered with the remaining membranes, was placed inside the abdominal cavity and the abdomen was closed to complete the transplantation.

Figure 4:
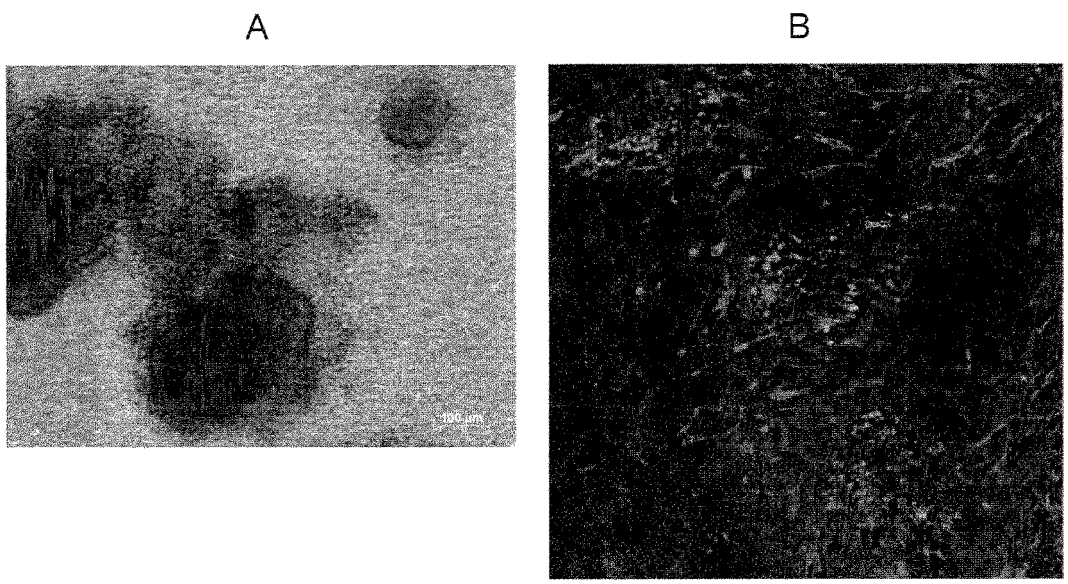
FIG. 4 shows a phase contrast micrograph (A) and an immunostaining image for insulin and CD31 (B) of a graft on day 14 after transplantation.

FIG. 4A shows a phase contrast microscope image of the graft transplanted in the mouse abdominal wall fat on day 14 after transplantation. FIG. 4B shows an image of the obtained artificial tissue immuno-stained (for CD31 and insulin) according to the routine procedure. In FIG. 4B, CD31-immunostaining positive areas (blood vessels, red color) were observed around insulin-immunostaining positive areas (pancreatic islets, green color) (indicating formation of vascularized pancreatic islets).

Figure 5:
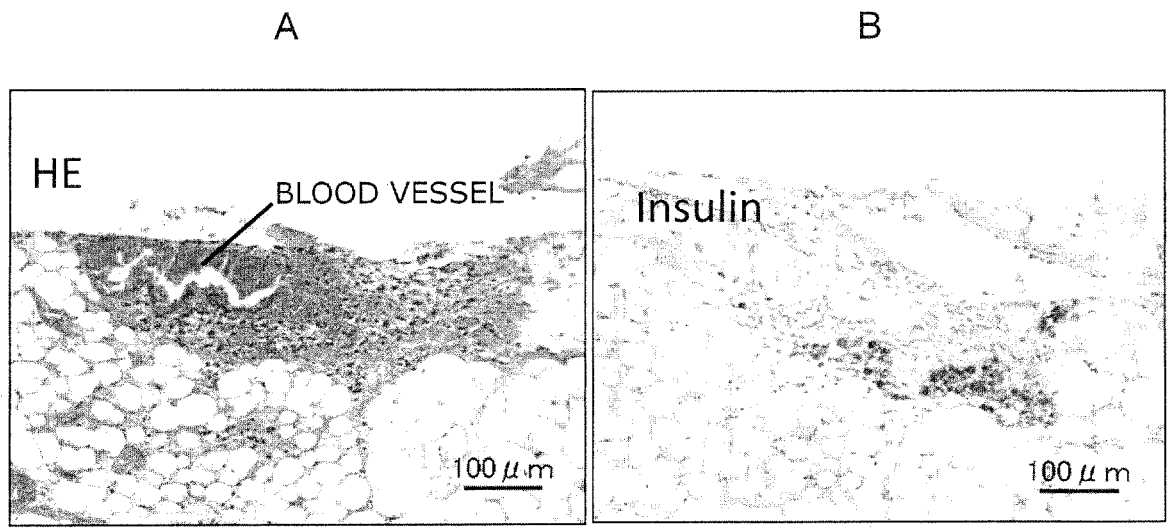
FIG. 5 shows a hematoxylin-eosin (HE) staining image (A) and an immunostaining image for insulin (B) of sections of a graft transplanted in the abdominal wall fat on day 14 after transplantation.

Sections of the graft transplanted in the mouse abdominal wall fat were prepared on day 14 after transplantation and subjected to HE staining and immunostaining (visualized by DAB staining) using anti-mouse insulin antibodies as a primary antibody to detect insulin. FIG. 5 shows a HE staining image. FIG. 5B shows an immunostaining image for insulin. The pancreatic islets survived in a state of being integrally attached to a cell layer constituted by the fibroblasts and the vascular endothelial cells. A vascular network and a blood stream (red blood cells) circulating inside the vascular network were confirmed in the layer of the cells. Further, secretion of insulin from the pancreatic islets was also confirmed.

Example 5

The present experiment was conducted to test if the artificial tissue of the present invention, which had been transplanted to the living body and survived, could actually lower a blood glucose level.

BALB/c mouse-derived mesenchymal stem cells (MSC) ($8\times10^5$ cells), and HUVEC ($1\times10^5$ cells), coated with fibronectin and gelatin, were seeded on a Transwell plate and cultured for 2 days. Then, 150 pancreatic islets just isolated from BALB/c mice were disposed on the cultured cells and cultured for 1 day to obtain an artificial tissue. Diabetes induced SCID mouse was subjected to laparotomy under inhalation anesthesia and the fat tissue attached to the left testicle was extended. The artificial tissue removed from the Transwell plate together with the membrane was placed on the extended fat tissue. Then, the artificial tissue, covered with the remaining fat tissue, was placed inside the abdominal cavity. The skin of the abdomen was closed to complete the operation. In a control group, 150 pancreatic islets wrapped with the above-mentioned fat tissue were transplanted. The transplantation of the pancreatic islets was performed to 4 mice, while the transplantation of the artificial tissue was performed to one mouse.

In the artificial tissue transplantation group, a blood glucose level became normal (200 mg/dL or lower) on day 14 after transplantation and it was further reduced to about 130 mg/dL on day 21. On the other hand, in the pancreatic islet transplantation group, a blood glucose level was not reduced lower than about 300 mg/dL even on day 21 after transplantation, thereby failing to become normal.

From these results, it was confirmed that the artificial tissue of the present invention could increase the secretion amount of insulin in response to glucose load and that the artificial tissue could survive in a living body to secrete the sufficient amount of insulin, thereby enabling to normalize the blood glucose level.

The invention claimed is:

1. A method for production of an artificial tissue, comprising:
    culturing fibroblasts and/or the cells capable of differentiating and vascular endothelial cells with a composition comprising fibronectin and gelatin, wherein the composition comprising fibronectin and gelatin coats the fibroblasts and/or the cells capable of differentiating and vascular endothelial cells; and
    culturing pancreatic islet cells arranged on a cell layer formed by the fibroblasts and/or the cells capable of differentiating and vascular endothelial cells; and
    forming a three-dimensional tissue structure by culturing the fibroblasts and/or cells capable of differentiating and the vascular endothelial cells with extracellular matrix, wherein the extracellular matrix is a combination of fibronectin and gelatin, wherein the extracellular matrix coats the three-dimensional tissue structure; and
    culturing pancreatic islet cells arranged on the three-dimensional tissue structure that has been formed, wherein:
    the fibroblasts and/or the cells capable of differentiating, the extracellular matrix, and the vascular endothelial cells constitute the three-dimensional tissue structure in which a vascular network structure has been formed; and
    the three-dimensional tissue structure contains pancreatic islets constituted by aggregating a plurality of the pancreatic islet cells.

2. A method for production of an artificial tissue, comprising:
    arranging and culturing fibroblasts and/or the cells capable of differentiating with a composition comprising fibronectin and gelatin, wherein the composition comprising fibronectin and gelatin coats the fibroblasts and/or the cells capable of differentiating; and
    culturing vascular endothelial cells on a cell layer formed by the fibroblasts and/or the cells capable of differentiating with a composition comprising fibronectin and gelatin, wherein the composition comprising fibronectin and gelatin coats the vascular endothelial cells; and
    forming a three-dimensional. tissue structure by culturing the fibroblasts and/or cells capable of differentiating and the vascular endothelial cells with extracellular matrix, wherein the extracellular matrix is a combination of fibronectin and gelatin, wherein the extracellular matrix coats the three-dimensional tissue structure; and
    culturing pancreatic islet cells arranged on the three-dimensional tissue structure that has been formed, wherein:
    the fibroblasts and/or the cells capable of differentiating, the extracellular matrix, and the vascular endothelial cells constitute the three-dimensional tissue structure in which a vascular network structure has been formed; and
    the three-dimensional tissue structure contains pancreatic islets constituted by aggregating a plurality of the pancreatic islet cells.

3. The method for production according to claim 1, wherein the pancreatic islets constituted by aggregating at least ten or more of the pancreatic islet cells.

4. The method for production according to claim 1, wherein stem cells are used as the cells capable of differentiating.

5. The method for production according to claim 2, wherein the pancreatic islets constituted by aggregating at least ten or more of the pancreatic islet cells.

6. The method for production according to claim 2, wherein stem cells are used as the cells capable of differentiating.

* * * * *